United States Patent [19]

Kelly, Jr.

[11] 4,344,303
[45] Aug. 17, 1982

[54] BEVERAGE CONTAINER COOLER

[76] Inventor: C. Brantley Kelly, Jr., 2615 Elk Grove Rd., Carrollton, Tex. 75006

[21] Appl. No.: 212,074

[22] Filed: Dec. 1, 1980

[51] Int. Cl.³ .............................................. F25D 3/08
[52] U.S. Cl. ...................................... 62/530; 62/371; 62/430; 62/457; 128/402; 150/2.3; 215/13 R; 220/902
[58] Field of Search ............ 220/902, 428; 215/13 R; 62/430, 457, 371, 372, 529, 530, 259.3, 331; 128/402, 399, 254; 150/2.1–2.6

[56] References Cited

U.S. PATENT DOCUMENTS

| | | | |
|---|---|---|---|
| 2,288,745 | 7/1942 | Sammis | 62/530 X |
| 2,547,886 | 4/1951 | Poux | 62/530 |
| 2,589,577 | 3/1952 | Rosenthal et al. | 62/530 X |
| 2,715,315 | 8/1955 | Giardini | 62/530 X |
| 2,961,124 | 11/1960 | Hunter et al. | 220/104 |
| 3,262,283 | 7/1966 | Taylor | 62/457 X |
| 3,285,455 | 11/1966 | Pewitt | 215/100.5 |
| 3,374,298 | 3/1968 | Studen | 264/41 |
| 3,807,194 | 4/1974 | Bond | 62/430 |
| 3,941,159 | 3/1976 | Toll | 138/147 |
| 4,114,759 | 9/1978 | Maloney | 206/523 |
| 4,183,226 | 1/1980 | Moore | 62/530 X |

FOREIGN PATENT DOCUMENTS

| | | | |
|---|---|---|---|
| 1401600 | 10/1968 | Fed. Rep. of Germany | 62/457 |
| 1111645 | 3/1956 | France | 62/371 |

Primary Examiner—Lloyd L. King
Attorney, Agent, or Firm—Kinney, Lange, Braddock, Westman and Fairbairn

[57] ABSTRACT

A cooling device has a flexible foam insulating layer with a cooling surface. A plurality of distinct cavities spaced from each other are located adjacent the cooling surface in the insulating layer. A cooling fluid is contained within each cavity. The device is cooled to freeze the cooling fluid, and an object such as a bottle is placed within the cooling device to be cooled.

8 Claims, 20 Drawing Figures

U.S. Patent  Aug. 17, 1982  Sheet 1 of 3  4,344,303
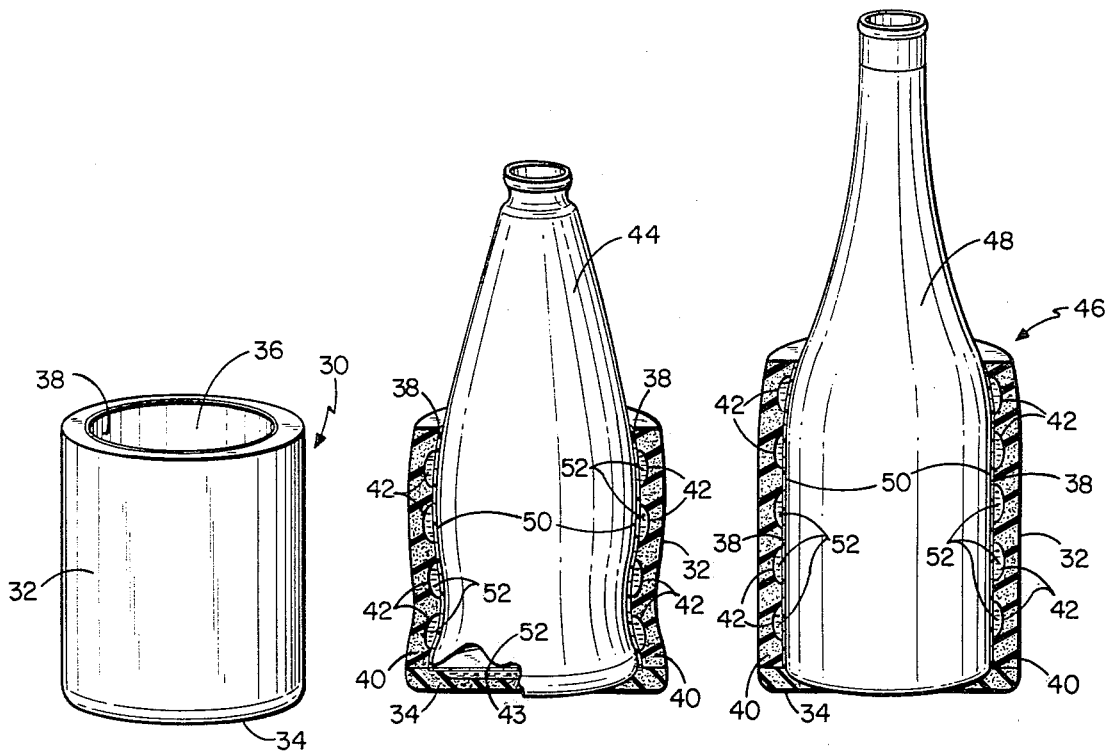
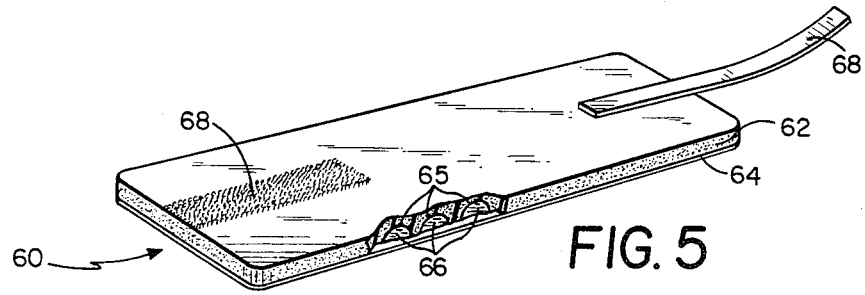
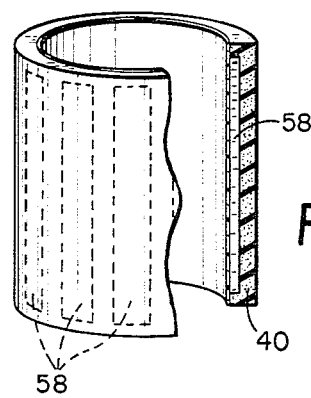
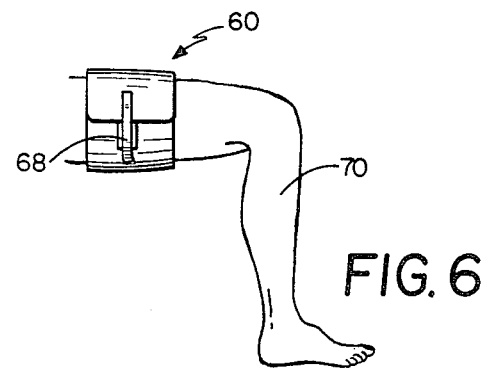

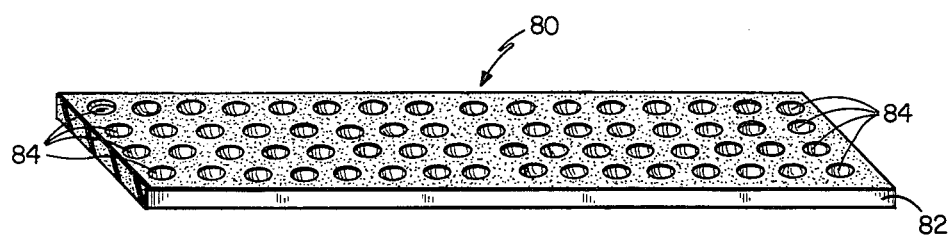
FIG. 7
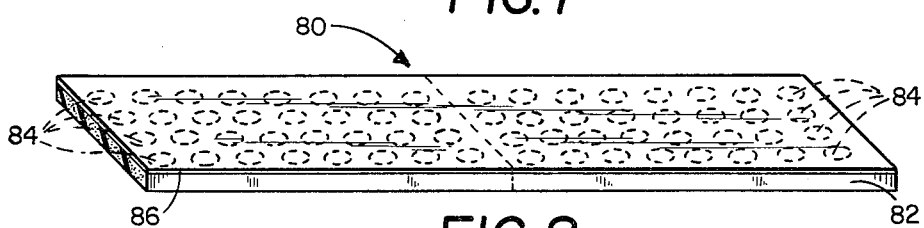
FIG. 8
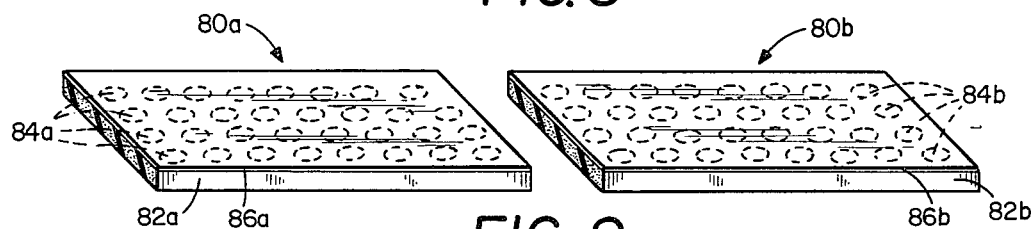
FIG. 9
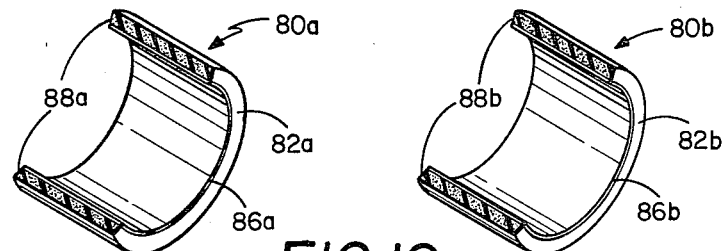
FIG. 10
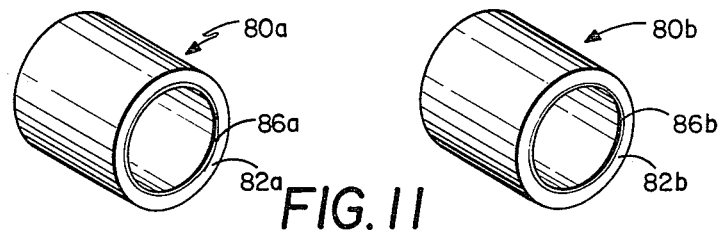
FIG. 11
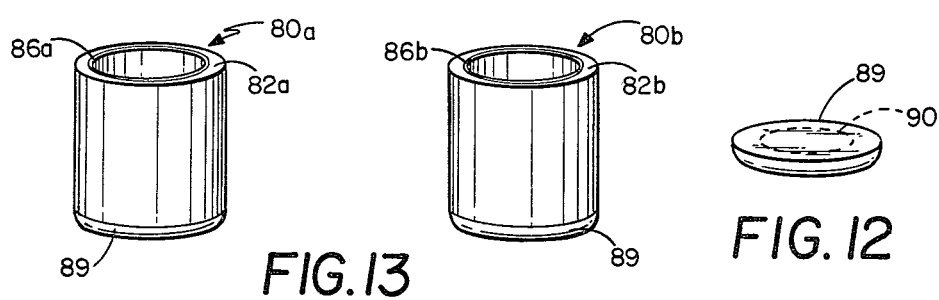
FIG. 12
FIG. 13

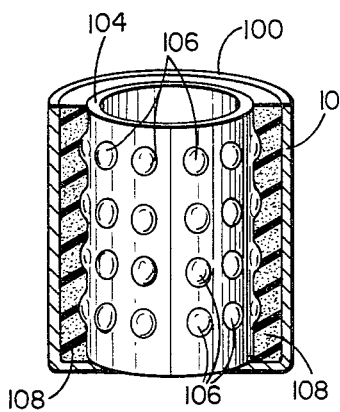
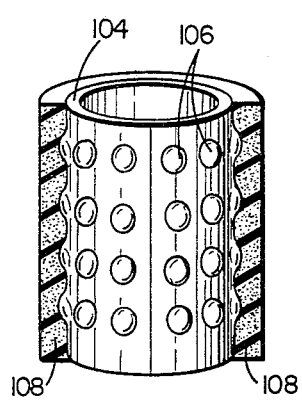
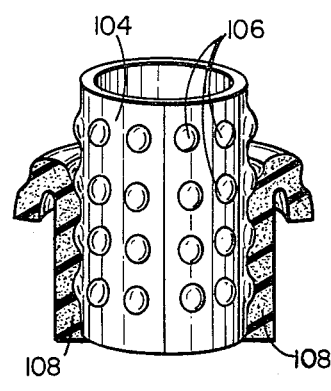
FIG.15  FIG.16  FIG.17
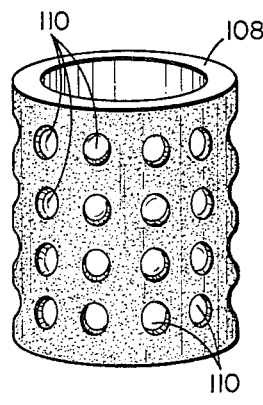
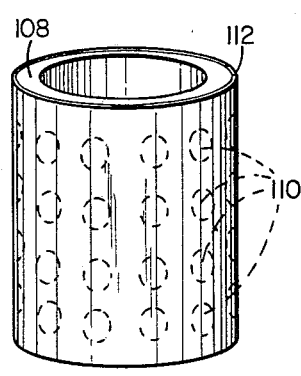
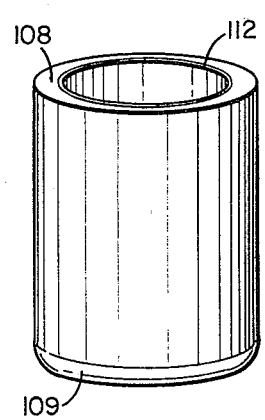
FIG.18  FIG.19  FIG.20
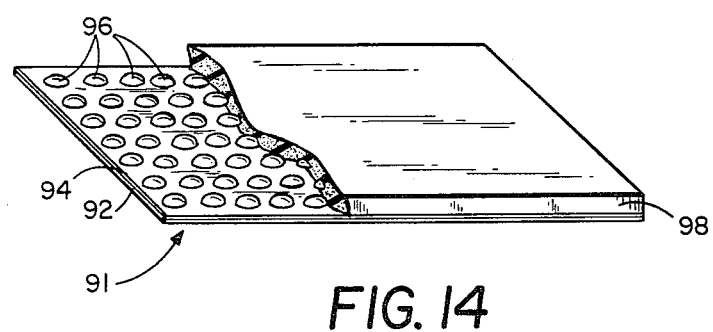
FIG.14

BEVERAGE CONTAINER COOLER

BACKGROUND OF THE INVENTION

1. Field of the Invention

The present invention relates to cooling devices. In particular, it relates to conductive cooling devices having pre-cooled fluids which extract heat from other objects.

2. Description of the Prior Art

Devices which cool or keep cool a beverage in a container by encompassing the container have become extremely popular. The cooling device is typically cylindrical in shape and is in the form of a cup in which the beverage container, a can or bottle, is placed. The cooling devices of the prior art have a rigid outside insulating layer usually made of polystyrene with a smooth rigid inner plastic liner. A refreezable gel in a continuous cavity is found between the polystyrene outer layer and the rigid plastic inner liner. A flexible plastic rim is attached to and encircles the opening of the cup for minimizing ambient air flow between the cup and the beverage container. One such cooling device is marketed by Freezesleeves of America, Inc. of Dallas, Tex.

There are several major disadvantages with the above-mentioned cooling devices. First, odd sized beverage containers will not fit within the cooling device. Thus, many types of beer bottles and wine bottles have to be kept cool in an inconvenient ice bucket. Moreover, irregularly shaped containers which do fit within the cooling device are inefficiently cooled, losing much of the cooling capacity to air circulating between the cooling device and the irregularly shaped container. Second, if the outer or inner layers of the cooling device are punctured, the refreezable gel will escape and the cooling device will lose its cooling capabilities. Third, an inconsistent cooling surface, affected by a gap in the frozen fluid, occurs whenever the cooling device is allowed to freeze in any non-vertical position.

SUMMARY OF THE INVENTION

The present invention includes a cooling device having a cooling surface and an elastic insulating layer. A plurality of distinct cavities spaced from each other are positioned adjacent the cooling surface, and are filled with a cooling fluid. The insulating layer is of sufficient thickness to provide insulative protection to the cooling fluid within the cavities and the beverage container from the ambient temperature.

The cooling device of the present invention is initially cooled, preferably to a frozen state. After cooling, a beverage container or the like is placed within the device adjacent the cooling surface, cooling the beverage within the container to a lower temperature. The elastic insulating layer permits the cooling device to be used with irregularly shaped and odd-sized containers and bottles since the elastic layer will expand to accommodate and conform to these containers. Even if one of the cavities of the present invention is punctured and the cooling fluid escapes, the puncture will not take away any significant cooling capabilities from the device since only the fluid from one cavity has escaped. The frozen cooling fluid in discrete cavities creates a consistent cooling surface regardless of the position at which the cooling device of the present invention is allowed to freeze.

BRIEF DESCRIPTION OF THE DRAWINGS

FIG. 1 is a perspective view of the cooling device of the present invention in a cup configuration.

FIG. 2 is a cross-sectional view of the cup configuration of the cooling device with an irregularly shaped beverage container shown whole.

FIG. 3 is a cross-sectional view of the cooling device in a cup configuration with a wine bottle shown whole.

FIG. 4 is a perspective view of the cup configuration with semi-cylindrical cavities with a portion broken away for better clarity.

FIG. 5 is a perspective view of a therapy wrap using the cooling device of the present invention.

FIG. 6 is an elevational view showing the therapy wrap of FIG. 5 on a leg.

FIGS. 7-13 are perspective views illustrating one preferred method of manufacturing the cup configuration of the cooling device of the present invention.

FIG. 14 is a perspective view with portions cut away for better clarity of another preferred method of manufacturing the cooling device of the present invention.

FIGS. 15-20 are perspective views of still another preferred method of manufacturing the cup configuration of the cooling device of the present invention.

DETAILED DESCRIPTION OF THE PREFERRED EMBODIMENTS

A preferred embodiment of the cooling device 30 of the present invention is illustrated in FIG. 1. The cooling device 30 is shown as a cylindrical cup having a cylindrical outer side wall 32 and a circular bottom 34. A beverage container is placed within chamber 36 of cup 30 so that the container is adjacent an inner cooling surface 38 of cooling device 30.

Cooling device 30, shown in cross-sectional form in FIGS. 2 and 3, has a flexible insulating layer 40 and a plurality of distinct cavities or pockets 42 adjacent the inner cooling surface 38. Preferably, insulating layer 40 is made of an elastic material such as a synthetic elastomer. In particular, insulating layer 40 preferably has a cellular structure to increase its thermal insulating factor. A preferred material for insulating layer 40 is a foam rubber such as a polyurethane rubber. The elastic property of insulating layer 40 permits device 30 to accept an irregular shaped container 44 and to conform to its surface. Inner cooling surface 38, therefore, provides more efficient extraction of heat from the container. A larger version 46 of cooling device 30 is shown in FIG. 3 conforming to the outer surfaces of wine bottle 48. The larger version 46 of the cooling device, due to the elasticity of insulating layer 40, will conform to virtually any shape of wine bottle in a particular volumetric size.

Cavities 42 are filled with any cooling fluid, preferably a freezable gel 52 of the type which is commonly known as "blue ice". Any gel or liquid which can be repeatedly frozen without deterioration is termed "cooling fluid" within this disclosure. Cavities or pockets 42 are individual and discrete cavities. In one successful embodiment twenty-eight individual cavities are provided. Although the cavities are shown as semi-hemispherical, the shape of cavities 42 is not critical to the practice of the present invention. Alternatively, the cavities can be semi-cylindrical cavities 58, the axis of the cylinder running along the vertical height of the entire insulating layer 40, as illustrated in FIG. 4, or the cavities may run horizontally, or can be any other configuration which still permits flexibility of the device when gel 52 is frozen.

Liner 50 is preferably attached to cooling surface 38 and is adjacent to cavities 42. Liner 50 is made of a flexible plastic which will not substantially impede the elastic quality of the insulating layer 40. A preferred plastic is polyvinyl chloride, but other flexible plastic films, such as polyethylene which do not become brittle at lower temperatures, are within the scope of the present invention.

Bottom 34 of cooling device 30 preferably contains any cooling fluid 52 in a cavity 43 similar to cavities 42 in insulating layer 40. Bottom 34 is made of the same material as insulating layer 42 and provides insulation to the bottom of the beverage container from the environment.

Another embodiment of the present invention is illustrated as cooling device 60 in FIGS. 5 and 6. Cooling device 60 is in the form of a relatively planar pad having an insulating layer 62 and liner 64 with cavities 65 filled with a cooling fluid 66. All elements of device 60 are made of the same materials as similar elements in the embodiments discussed previously. Fastener 68 is attached to the outside surface of pad 60 to retain pad 60 in place. Pad 60, when precooled, can be used as a therapy wrap around a body limb, such as leg 70, as shown in FIG. 6. In addition, pad 60 can be wrapped around other objects to be cooled, including bottles, cans, boxes and the like. Fastener 68 is preferably a Velcro fastener manufactured by I. E. Dupont de Nemours & Co. of Wilmington, Del.

The cylindrical cup form of the cooling device of the present invention can be made by several methods of manufacture. In one method of manufacture, as illustrated in FIGS. 7 through 13, a sheet 80 of foam rubber has been extruded, cast of molded in a conventional manner forming insulating layer 82. Cavities 84 have been cast or molded with sheet 80 or have been formed by embossing sheet 80 using an embossing roll.

Cooling fluid is then placed into the cavities, and a layer or sheet of plastic film 86 is used as a liner to seal the fluid into cavities 84. Liner 86 may be attached to insulating layer 82 by any of several methods, including adhesive bonding, heat welding or sonic welding. Fasteners can be attached to sheet 80 in its present state to the outside of the insulating layer 82 to form a flexible therapy wrap, as previously described and shown in FIGS. 5 and 6.

If the cup form of the cooling device is desired, sheet 80 is cut into smaller sections 80a and 80b, as illustrated in FIG. 9. It should be understood that sheet 80 can be of any length, and can be cut into any number of sections which are of appropriate size for the use intended, but only two sections 80a and 80b are shown in the Figures for purposes of illustration.

Individual sections 80a and 80b are then formed into cylinders, as shown in FIGS. 10 and 11. Ends 80a and 80b are permanently attached by any number of conventional manufacturing methods, such as adhesives, heat or sonic welding. A bottom 89 having a cavity 90 filled with cooling fluid shown in FIG. 12. is then attached to one of the ends of sections 80a and 80b, now cylinders, by any of the conventional manufacturing methods described above. Finished sections 80a and 80b are shown in their cup forms in FIG. 13.

Another method of forming a sheet of the cooling device is shown in FIG. 14. Two sheets 92 and 94 are laminated together with cavities 96 inbetween filled with cooling fluid to form laminated sheet 91. Insulating layer 98 is then formed onto the laminated sheet 91 which contains the cooling fluid.

One preferred method of forming laminated sheet 91 is by forming cavities within sheet 94, filling the cavities with cooling fluid and then laminating a top sheet 92, shown as the bottom sheet, to seal the cavities. After insulating layer 98 is formed onto sheet 91, then sheet 91 can be processed by the steps described in FIGS. 9 through 13 to form the cup-type configuration of the cooling device.

A third method of forming the cup-type configuration of the cooling device by molding is illustrated in FIGS. 15–20. Mold 100 has outer shell 102 and inner cylindrical core 104 with a plurality of protruding knobs 106. Inner cylindrical core 104 is spaced coaxially within outer shell 102. Preferably, a foam rubber is injected into the space between inner core 104 and outer shell 102 to form insulating layer 108 in a cylindrical form. Knobs 106 form cavities within insulating layer 108 which are layer filled with a cooling fluid.

In FIG. 16 outer shell 102 has been removed, exposing cured foam rubber insulating layer 108. Insulating layer 108 can then be removed from the inner core 104 by turning the cured insulating layer inside-out similar to taking a sock off a leg, as illustrated in FIG. 17. An alternative method of removing insulating layer 108 from inner core 104 is to provide a collapsible inner core 104 that collapses inwardly to separate itself from the insulating layer 108. FIG. 18 shows the insulating layer 108 turned inside-out with cavities 110 which had been formed by outwardly protruding knobs 106. A flexible liner 112 is laminated to the outside surfaces of cured insulating layer 108 sealing the cavities 110, as shown in FIG. 19. The cured insulating layer 108 with the laminated liner 112 is then turned again inside-out resulting in the finished cup configuration, illustrated in FIG. 20 with a bottom 109 having been added in the manner previously discussed. The cavities 110 are then filled by preferably piercing the foam rubber, injecting cooling fluid and sealing the exterior with a soft and flexible plastic coating.

In normal use, the cup configuration of the cooling device of the present invention is placed in a freezer and the cooling fluid allowed to freeze. The cup is flexible when frozen since the insulating layer and inner liner are made of materials which are flexible at lower temperatures and the frozen cooling fluid is contained in discrete spaced apart cavities. Since the foam rubber insulating layer of the cup is elastic, it allows the cup to conform to the shape of the beverage container while permitting the cavities with the frozen cooling fluid to be closely adjacent to the surface of the beverage container. The close fit of the cup to the beverage container prevents flow of any atmospheric air between the cup and the beverage container resulting in a cooler beverage in the beverage container and a more efficient heat transfer device. The conforming fit of the cup also has the advantage of fitting odd sized and irregularly shaped containers in a similar manner. The capability of conforming to the container is of great value in the case of wine and champagne bottles which occur in many different shapes within one volumetric size.

The foam rubber insulating layer has a further advantage in aiding a user to grip the cup with the beverage container. Foam rubber may be squeezed and is tackier than rigid plastics such as polystyrene. The flexible liner, which is made of a smooth plastic, allows the beverage container to be placed within the cup while avoiding direct contact between the container and the foam rubber.

If the cooling device of the present invention becomes punctured, only the cavity that is punctured losses its cooling capability. The rest of the refreezable fluid-filled cavities will still function as intended, since the cavities are discrete.

The consistent cooling surface affected by discrete cooling cells enables the user of the present invention to disregard the position at which the cooling device is placed in a freezer. This offers the further advantage of convenience to the user of the present inventor's cooling device.

Although the present invention has been described with reference to embodiments of a cooling cup device and therapy wrap, persons skilled in the art will recognize that changes may be made in form and detail for uses not described herein without departing from the spirit and scope of the invention.

What is claimed is:

1. A flexible cooling device capable of conforming to irregular shaped surfaces comprising:
    an elastic insulating layer having a cooling surface;
    a plurality of discrete sealed cavities spaced from each other with sufficient portions of the elastic layer between the spaced cavities to provide sufficient flexibility to allow the cooling surface to conform to irregular shaped surfaces and imbedded in the insulating layer adjacent the cooling surface; and
    a cooling fluid for freezing within the cavities.

2. The cooling device of claim 1 and further comprising a flexible liner attached to the cooling surface of the elastic insulating layer.

3. The device of claim 2 wherein the flexible liner is made of a flexible synthetic plastic.

4. The device of claims 1 or 2 wherein the insulating layer is in a cylindrical configuration with the cooling surface forming an inside surface of the cylinder and having one end capped with an insulating material, the device having a cup configuration.

5. The device of claim 1 and further comprising fastening means for retaining the cooling device on an object to be cooled, the fastening means being attached to a surface opposite the cooling surface such that when the device is placed around the object the cooling surface is adjacent to the object.

6. The device of claim 1 wherein the insulating layer is made of a foam rubber.

7. The device of claim 1 wherein the cooling fluid is a refreezable gel.

8. The device of claim 1 wherein the cooling fluid is a refreezable fluid.

* * * * *